(12) United States Patent
Blum et al.

(10) Patent No.: US 7,991,466 B2
(45) Date of Patent: Aug. 2, 2011

(54) METHOD AND APPARATUS TO STIMULATE CELL INITIATED NITRIC OXIDE (NO) ACTIVATION, INTERSTITIAL PROTEIN CLEARANCE, AND ANGIOGENESIS

(75) Inventors: Kenneth Blum, San Diego, CA (US); William J. Heaney, Huntington Beach, CA (US); Roger L. Waite, San Diego, CA (US)

(73) Assignee: Electronic Waveform Lab, Inc., Huntington Beach, CA (US)

( * ) Notice: Subject to any disclaimer, the term of this patent is extended or adjusted under 35 U.S.C. 154(b) by 463 days.

(21) Appl. No.: 12/252,271

(22) Filed: Oct. 15, 2008
(Under 37 CFR 1.47)

(65) Prior Publication Data

US 2009/0240304 A1    Sep. 24, 2009

Related U.S. Application Data

(60) Provisional application No. 60/980,737, filed on Oct. 17, 2007.

(51) Int. Cl.
*A61N 1/00* (2006.01)

(52) U.S. Cl. .......................................................... 607/2
(58) Field of Classification Search .................... 607/2
See application file for complete search history.

(56) References Cited

U.S. PATENT DOCUMENTS 7,727,221 B2 * 6/2010 Penner et al. ................. 604/500

* cited by examiner

*Primary Examiner* — George Manuel
(74) *Attorney, Agent, or Firm* — Blakely, Sokoloff, Taylor & Zafman

(57) ABSTRACT

Methods and apparatus to restore central and peripheral disorders/dysfunction caused by edema, ischemia, and nitric oxide (NO) deficiency and to improve or facilitate muscle performance (e.g. endurance and recovery) by utilizing a device which stimulates cell initiated NO activation, promotes interstitial protein clearance, and induces angiogenesis. By use of these methods and apparatus, it is possible to treat a number of disorders/diseases caused by a deficiency of nitric oxide, a lack of proper circulation and vascularity, a build up of proteins and increased tissue water content due to injury; and to improve or facilitate muscle performance (e.g., muscle endurance and muscle recovery).

19 Claims, 1 Drawing Sheet

US 7,991,466 B2

METHOD AND APPARATUS TO STIMULATE CELL INITIATED NITRIC OXIDE (NO) ACTIVATION, INTERSTITIAL PROTEIN CLEARANCE, AND ANGIOGENESIS

CROSS-REFERENCE TO RELATED APPLICATION

The present application claims priority of provisional application 60/980,737, filed Oct. 17, 2007.

BACKGROUND OF THE INVENTION

An H-Wave® device was developed in 1981 by Electronic Waveform Lab., Inc. as an alternative electrotherapeutic device to reduce pain and stimulate muscles. Pain relief is obtained by stimulating nerves to shut down and/or fatigue the sodium pump within the nerve, which creates an anesthetic or analgesic effect. Muscles can also be contracted to increase circulation, improve range of motion, prevent atrophy, re-educate muscle, prevent venous thrombosis, and reduce muscle spasm. These benefits were created by a physical muscle pump that would squeeze and relax muscles to help circulation and create muscle activity.

The H-Wave® device has been used during painful episodes or after injury to manage symptoms. Typically, the device would be used for 30 minutes to address symptoms as needed. Four to six electrodes would be applied around the painful site or injured area. The device would be used for 30 minutes or until the symptoms were reduced. Treatments would be repeated when pain or symptoms were present.

SUMMARY OF INVENTION

A device which referred to herein as H-Wave® device, is a unique electrotherapeutic stimulator having differentiating characteristics which when used in a particular manner operates to stimulate nitric oxide (NO) activation, promote interstitial protein clearance, and induce angiogenesis in order to benefit the body in numerous applications. The device can be used to treat chronic soft tissue neuropathic and other inflammatory conditions and a number of disorders/diseases caused by a deficiency of NO, edema and ischemia. Since it operates with unique characteristics including the above cited actions and is used to decrease protein build up, and increase oxygenation, it differs from other basic electrotherapeutic devices (e.g., Tens, etc). Research has uncovered several new uses for this device.

1) Specific application of this device results in a cell initiated increase in NO, angiogenesis and protein clearance. These simultaneous reactions to specific application of the H-Wave® device can be of benefit to many health related issues.

2) Specific application of this device on healthy patients and muscles results in improved muscle performance (e.g. improved endurance and muscle recovery).

DETAILED DESCRIPTION OF THE INVENTION

Figure 1:
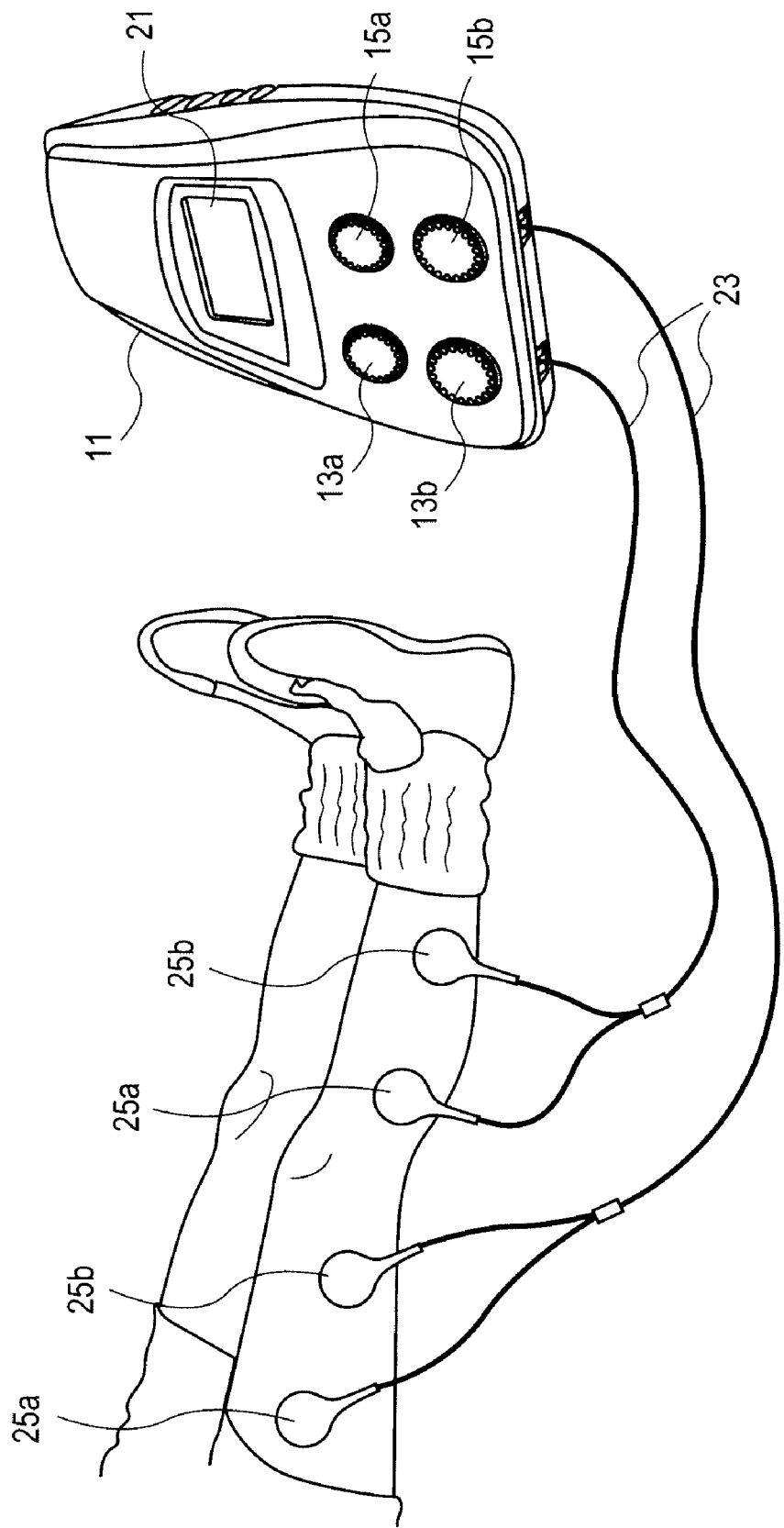
FIG. 1 shows a use of the device according to the invention.

A method is described to use a device to apply an electronic current to flow through a body tissue region, for a period of time, applied to electrodes of the device sufficient to stimulate nitric oxide (NO) activation (e.g. synthesis, receptor sensitivity, etc.), enhanced protein clearance and provide an angiogenic response in the region of damaged or healthy tissue. The electronic current found in such device, known as an H-Wave® device, has the following characteristics. A bipolar exponentially decaying pulse with a frequency between 1 Hz and 70 Hz, a voltage between 1 volt and 200 volts, a current between 1 mA and 200 mA, and a pulse duration between 3 milliseconds and 15 milliseconds. In a typical use, the exponentially decaying pulse has a frequency of about 1 Hz. The voltage is about 35 volts. The current is about 35 mA. The pulse duration is about 5 milliseconds. References to H-Wave® device herein should be understood to mean any device which produces a pulse having the above described characteristics.

In one embodiment, the H-Wave® device has three independent channels. In another embodiment, the device has two independent channels. One pair of electrodes is attached to each channel. The number of channels and electrode pairs is not important, as only one channel and electrode pair is needed to implement the invention. Additional channels and electrode pairs allow additional portions of the body to be treated simultaneously or to provide additional stimulus to a desired body region.

Referring to FIG. 1, which shows a typical two channel H-Wave® device 11, each channel is controlled by corresponding frequency and intensity setting via knobs 13a, 13b and 15a, 15b, respectively. In this connection, intensity generally refers to voltage, but increasing voltage also changes the current depending on the amount of resistance between the two electrodes. Display 21 shows the current frequency and voltage settings. The frequency controls the number of pulses per second. The intensity controls the output voltage. In one embodiment, the device is battery powered and may include an internal rechargeable battery pack. Alternatively, the device may be powered by ordinary household current. A set of lead wires 23 is attached to the device for each channel. These wires are approximately six feet long and connect to self adhesive electrodes 25a and 25b that are placed on the skin. Each channel connects with and controls two electrodes, i.e., one electrode pair as noted above. The signal runs between the two electrodes of a particular channel. Each channel is independent, so each channel can be used on a different muscle or area, or multiple channels can be applied to the same muscle or area.

The invention is directed to new methods of use of the H-Wave® device as a treatment modality for chronic soft tissue neuropathic and other inflammatory conditions and a number of disorders/diseases caused by a deficiency of NO, protein build up, and a lack of circulation, vascularity, and oxygenation effecting three basic areas: 1) vascular disorders, 2) edema and 3) ischemia. The new uses include: 1) specific application of this device to result in a cell initiated increase in NO, angiogenesis and protein clearance. These simultaneous reactions to specific application of the H-Wave® device can be of benefit to many health related issues. 2) Specific application of this device on healthy patients and muscles results in improved muscle performance (e.g. improved endurance and muscle recovery).

One new method of use involves the use of the H-Wave® device as a stimulator of NO activation, a promoter of interstitial protein clearance and an inducer of angiogenesis for conditions relating to the above described three basic areas, i.e., vascular disorders, 2) edema and 3) ischemia. A second new method of use involves the use of the H-Wave® device as a stimulator of NO activation, a promoter of interstitial protein clearance and an inducer of angiogenesis for improved muscle performance such as improved muscle recovery time and to improve muscle endurance.

Vascular disorders include aneurysm, angiomatosis, basal ganglia hemorrhage, carotid artery diseases, coronary diseases, embolism, hemorrhoids, hypertension, hypotension and splenic infarction.

Edema disorders include angioneurotic edema, myxedema, scleredema adultorum.

Ischemia disorders include ischemia (generalized), shock, cardiogenic, angina, optic neuropathy.

The device enables cell initiated increased NO activation, induced angiogenesis and protein clearance which also creates applications in areas such as fracture healing, non union fracture treatment, erectile dysfunction and other ailments which benefit from increased NO activation, induced angiogenesis and protein clearance To obtain NO activation, angiogenesis, and protein clearance, the H-Wave® device is applied with the following specific guidelines.

The treatment location will be based on where the patient has a lack of (or need for) vascularity, NO activation, and a build up of proteins. The two largest muscles surrounding this location will be used. One channel of the H-Wave® device is used on each muscle. A path for the treatment is established by placement of an electrode at the insertion and end point of each muscle. Only a minimum frequency setting of 1-5 Hz is used. The intensity level (voltage/current) must be raised to a level high enough to obtain a strong visible contraction. The exact intensity dial level varies from patient to patient and the spacing and placement of the electrodes.

The treatment should be applied for a minimum of 30-60 minutes for each session, and should be applied daily for at least three weeks. To accomplish the above mentioned results, treatment should not be based on activity or symptoms, but rather a regular daily treatment schedule continuing indefinitely for chronic or permanent situations. For non-chronic or non-permanent situations, daily treatment should continue until complete healing or resolution of the problem, and should not stop based on the ups and downs of symptoms.

To improve muscle performance (e.g. muscle endurance and muscle recovery) the H-Wave® device is applied with these new specific guidelines.

When improving muscle performance, damaged or injured tissues should be avoided. Electrodes are placed at the insertion and end points of each target muscle. Only a minimum frequency setting of 1-5 Hz is used. The intensity must be raised to a level high enough to obtain a strong visible contraction. The treatment should be applied for a minimum of 30 minutes for each session, and should be applied daily for at least three weeks.

When being used for recovery, the device should be applied directly after the athletic or strenuous activity, rather than waiting for any symptoms to arise. Electrodes are placed at the insertion and end points of each target muscle. Only a minimum frequency setting of 1-5 Hz is used. The intensity must be raised to a level high enough to obtain a strong visible contraction. One 60 minute session should be given directly after activity. The first day after activity at least one 60 minute session or two 30 minute sessions should be provided. This should continue daily until the person being treated is completely recovered.

When being used for improved endurance, the device should be applied before athletic or strenuous activity and on a body without current injury. Electrodes are placed at the insertion and end points of each target muscle. Only a minimum frequency setting of 1-5 Hz is used. The intensity must be raised to a level high enough to obtain a strong visible contraction. One 60 minute session should be given before activity, but on the day of activity. For more profound results the device should be used daily for 60 minutes per day. Treatments should be given proactively without waiting for any symptoms and regardless of daily activities or exercise levels.

When being used to regenerate damaged living tissue resulting from an injury, the device should be applied by determining the borders of the damaged tissue. The living tissue which can be regenerated includes skin, ligaments, bone, cartilage, and muscle. A path is set defined by the borders, i.e., the portions of healthy tissue which surround the damage tissue. One of the channels should be placed so that the electrodes are oriented with respect to the region of damaged tissue based on the path so that the electrodes are spaced approximately equally distant from each other around the damaged tissue area. Another channel should be placed so that the electrodes are oriented at the insertion and end point of the largest muscle in the area of damaged tissue. Only a minimum frequency setting of 1-5 Hz is used. The intensity level should be set as high as possible without causing pain. That is, the intensity level is slowly increased until there is evidence of strong muscle contraction or the person receiving the treatments first starts to feel any discomfort at which point the intensity should be reduced until there is no discomfort. The treatment should be applied for a minimum of 30 minutes for each session and continue until the wound healing or recovery has been completed. There should be at least one session per day. That is, the electrical pulse should have a magnitude sufficient to cause a discontinuous electronic current to flow through the tissue region, for a period of delivery sufficient to stimulate nitric oxide activation, enhanced protein clearance and an angiogenic response in the region of damaged tissue.

To facilitate improved fracture healing and allow for healing of non-union fractures the H-Wave device is applied using the following guidelines.

One pair of electrodes is placed directly across the fracture. Other pairs of electrodes are placed on the muscles groups surrounding the fracture site. Only a minimum frequency setting of 1-5 Hz is used. The intensity level (voltage/current) must be raised to a level in which the muscle contractions can be felt by the patient, but not high enough to cause pain or movement of the fractured bone. The exact intensity dial level varies from patient to patient and the spacing and placement of the electrodes.

The treatment should be applied for a minimum of 2 hours per day and up to 20 hours per day with each session lasting between 1 and 4 hours. The skin under electrodes should be checked at least every 4 hours for irritation. If irritation occurs the electrode placement should be adjusted slightly to avoid irritated areas of skin. Treatment is applied daily until the fracture is healed.

The foregoing description sets forth a treatment protocol for stimulating a cell-initiated activation of nitric oxide, enhanced protein clearance and angiogenic response in living cells. Specific examples are set forth in order to assist in a complete understanding of the invention. However, the invention is not limited by the specific examples and is intended to cover all such treatment protocols, and is limited only as defined by the following claims.

We claim:

1. An electrical stimulation apparatus for delivering an electrical field over a predetermined period of time to a targeted body tissue in order to stimulate a cell-initiated activation of nitric oxide, enhanced protein clearance and angiogenic response in living cells within the targeted body tissue, the electrical stimulation apparatus comprising:

a) a plurality of electrodes adapted to deliver an electrical field to the targeted body tissue;
b) a control mechanism controlling an amplitude and a duration of a period of delivery of electrical pulses from the power supply to the plurality of electrodes such that when the plurality of electrodes are disposed in proximity with the targeted body tissue at a plurality of locations, the electrical field is generated between the electrodes, wherein an intensity of the electrical field delivered to the targeted body tissue through the electrodes and the duration of the period of delivery is sufficient to stimulate nitric oxide (NO) activation, enhanced protein clearance and an angiogenic response in the targeted body tissue.

2. The electrical stimulation apparatus of claim 1, wherein the electrode placement includes any area of the body in which muscle or electrically active tissue is present.

3. The electrical stimulation apparatus of claim 1, wherein the electrical field has the following characteristics:
   a) a bi-polar exponentially decaying pulse;
   b) a frequency between 1 Hz and 5 Hz;
   c) a voltage between 1V and 200V;
   d) a current between 1 mA and 200 mA; and
   e) a pulse duration between 3 milliseconds and 15 milliseconds.

4. An electrical stimulation apparatus for delivering an electrical field over a predetermined period of time to a targeted healthy body tissue in order to stimulate a cell-initiated activation of nitric oxide, enhanced protein clearance and an angiogenic response in living cells within the targeted healthy body tissue, the electrical stimulation apparatus comprising:
   a) a plurality of electrodes adapted to deliver an electrical field to the targeted body tissue;
   b) a control mechanism controlling an amplitude and a duration of a period of delivery of electrical pulses from the power supply to the plurality of electrodes such that when the plurality of electrodes are disposed in proximity with the targeted healthy body tissue at a plurality of locations, the electrical field is generated between the electrodes, wherein an intensity of the electrical field delivered to the healthy targeted body tissue and the duration of the period of delivery is sufficient to stimulate nitric oxide (NO) activation, enhanced protein clearance and an angiogenic response in the healthy targeted body tissue to improve muscle performance by inducing a recovery of the tissue following exercise or activity and to enhance endurance.

5. The electrical stimulation apparatus of claim 4, wherein the electrode placement includes any area of the body in which muscle or electrically active tissue is present.

6. The electrical stimulation apparatus of claim 4, wherein the electrical field has the following characteristics:
   a) a bi-polar exponentially decaying pulse;
   b) a frequency between 1 Hz and 5 Hz;
   c) a voltage between 1V and 200V;
   d) a current between 1 mA and 200 mA; and
   e) a pulse duration between 3 milliseconds and 15 milliseconds.

7. A method for regenerating damaged living tissue resulting from an injury by stimulating a cell-initiated activation of nitric oxide, enhanced protein clearance and angiogenic response in living cells within the damaged living tissue, said method comprising:
   (a) determining a path in the region of the damaged living tissue;
   (b) placing and orienting at least one pair of electrodes with respect to the region of damaged living tissue based on the determined path; and
   (c) applying to the at least one electrode pair electrical pulses which generate an electric field which flows through the damaged living tissue region, said electric field having an intensity and period of delivery sufficient to stimulate nitric oxide (NO) activation, enhanced protein clearance and an angiogenic response in the region of the damaged living tissue.

8. The method of claim 7 wherein said period of delivery is a minimum of 30 minutes per session and there is at least one session per day.

9. The method defined by claim 7 wherein the electrical field has the following characteristics:
   a) a bi-polar exponentially decaying pulse;
   b) a frequency between 1 Hz and 5 Hz;
   c) a voltage between 1V and 200V;
   d) a current between 1 mA and 200 mA; and
   e) a pulse duration between 3 milliseconds and 15 milliseconds.

10. A method for stimulating a cell-initiated activation of nitric oxide, enhanced protein clearance and an angiogenic response in living cells within a targeted healthy tissue region, said method comprising:
    (a) determining a path in the region of the targeted healthy body tissue;
    (b) placing and orienting at least one pair of electrodes with respect to the targeted healthy tissue region based on the determined path; and
    (c) applying to the at least one pair of electrodes electrical pulses which generate an electric field which flows through the targeted healthy living tissue region, said electric field having an intensity and period of delivery sufficient to stimulate nitric oxide (NO) activation, enhanced protein clearance and an angiogenic response in the healthy targeted body tissue to induce improved muscle performance by a recovery of the tissue following exercise or activity and to enhance endurance during exercise or activity.

11. The method defined by claim 10 wherein said method is used for muscle recovery after athletic or strenuous activity, said period of delivery is one 60 minute session given directly after activity and during the first day after activity at least one 60 minute session is performed or two 30 minute sessions are performed.

12. The method defined by claim 10 wherein said method is used for improved endurance, and said period of delivery is one 60 minute session before activity on the day of activity.

13. The method defined by claim 10 wherein the electrical field has the following characteristics:
    a) a bi-polar exponentially decaying pulse;
    b) a frequency between 1 Hz and 5 Hz;
    c) a voltage between 1V and 200V; and
    d) a current between 1 mA and 200 mA.

14. A method for fracture healing and the healing of non-union fractures in a patient by stimulating a cell-initiated activation of nitric oxide, enhanced protein clearance and an angiogenic response in living bone tissue cells, said method comprising:
    a) placing one pair of electrodes directly across a fracture;
    b) placing at least a second pair of electrodes on at least one muscle group surrounding the fracture site;
    c) applying to each pair of electrodes electrical pulses which generate an electric field which flows through said electrodes, said electric field having an intensity and period of delivery sufficient to stimulate nitric oxide (NO) activation, enhanced protein clearance and an angiogenic response in said living bone tissue.

15. The method defined by claim 14 wherein said electrical pulses have a frequency of 1-5 Hz and said intensity is at a level in which the muscle contractions can be felt by the patient, but not high enough to cause pain or movement of the fractured bone.

16. The method defined by claim 14 wherein said applying is performed in sessions of 1 to 4 hours, such that in a 24 hour period of time there is a minimum of 2 hours of said applying.

17. The method defined by claim 14 wherein the electrical field has the following characteristics:
   a) a bi-polar exponentially decaying pulse;
   b) a frequency between 1 Hz and 5 Hz;
   c) a voltage between 1V and 200V;
   d) a current between 1 mA and 200 mA; and
   e) a pulse duration between 3 milliseconds and 15 milliseconds.

18. A method for stimulating a natural process to stimulate a cell-initiated activation of nitric oxide, enhanced protein clearance and angiogenic response in living body tissue, said method comprising:

(a) determining a path in the living body tissue;
(b) placing and orienting said electrodes with respect to living body tissue based on the determined path; and
(c) impressing across the electrodes electrical pulses which generate an electric field which flows through the living body tissue region, said electric field having an intensity and period of delivery sufficient to stimulate nitric oxide (NO) activation, enhanced protein clearance and an angiogenic response in the living body tissue.

19. The method defined by claim 18 wherein the electrical field has the following characteristics:
   a) a bi-polar exponentially decaying pulse;
   b) a frequency between 1 Hz and 5 Hz;
   c) a voltage between 1V and 200V;
   d) a current between 1 mA and 200 mA; and
   e) a pulse duration between 3 milliseconds and 15 milliseconds.

\* \* \* \* \*